United States Patent [19]

Farng et al.

[11] Patent Number: 4,784,780
[45] Date of Patent: Nov. 15, 1988

[54] LUBRICANT ADDITIVE COMPRISING MIXED HYDROXYESTER OR DIOL/PHOSPHORODITHIOATE-DERIVED BORATES

[75] Inventors: Liehpao O. Farng, Lawrenceville; Andrew G. Horodysky, Cherry Hill, both of N.J.

[73] Assignee: Mobil Oil Corporation, New York, N.Y.

[21] Appl. No.: 189,869

[22] Filed: May 3, 1988

Related U.S. Application Data

[63] Continuation-in-part of Ser. No. 98,339, Sep. 18, 1987, abandoned.

[51] Int. Cl.$^4$ ........................................... C10M 137/10
[52] U.S. Cl. ............................ 252/32.7 E; 252/49.6; 252/400.2; 252/400.41; 568/2
[58] Field of Search ............. 252/32.7 E, 49.6, 400.41, 252/400.2; 568/2

[56] References Cited

U.S. PATENT DOCUMENTS

| | | | |
|---|---|---|---|
| 3,192,162 | 6/1965 | Bartlett | 252/46.6 |
| 4,450,096 | 5/1984 | Horodysky | 252/32.7 |
| 4,555,353 | 11/1985 | Horodysky | 252/49.6 |
| 4,584,115 | 4/1986 | Davis | 252/49.6 |
| 4,600,517 | 7/1986 | Doner et al. | 252/32.7 E |
| 4,600,520 | 7/1986 | Horodysky | 252/49.6 |

*Primary Examiner*—Jacqueline V. Howard
*Attorney, Agent, or Firm*—Alexander J. McKillop; Michael G. Gilman; Van D. Harrison, Jr.

[57] ABSTRACT

Disclosed herein are the reaction products of dialkyl or diaryl phosphorodithioate acids and hydrocarbyl diols, hydroxyester or related polydiols and borating agent. These reaction products are useful as additives for lubricating compositions.

40 Claims, No Drawings

LUBRICANT ADDITIVE COMPRISING MIXED HYDROXYESTER OR DIOL/PHOSPHORODITHIOATE-DERIVED BORATES

This is a continuation-in-part application of our co-pending application, Ser. No. 098,339, filed Sept. 18, 1987 now abandoned, which is incorporated herein by reference.

NATURE OF THE INVENTION

This invention is concenred with the borate compounds of mixed hydroxyester or diol/phosphorodithioates and lubricant compositions containing these materials.

SUMMARY OF THE INVENTION

In one aspect this invention comprises the reaction product resulting from the reaction of phosphorodithioate-drived alcohols which are co-borated with hydrocarbyl diols, hydroxyesters, or related polydiols. In another aspect this invention comprises the lubricant composition made from the afore described reaction product and a liquid hydrocarbon liquid.

DESCRIPTION OF PREFERRED EMBODIMENT

The first step in the preparation of the reaction products of this invention is to obtain the O,O-dialkyl or O,O-diaryl phosphorodithioic acid by the reacting an alcohol or hydrocarbyl phenol with phosphorus pentasulfide, according to the following schematic formulas:

$$ROH + R_2S_5 \rightarrow 2(RO)_2PSSH + H_2S \qquad I$$

Where R is $C_3$ to $C_{30}$ hydrocarbyl or oxyhydrocarbylene radical, or mixtures thereof and optionally contains sulfur, oxygen, and nitrogen atoms. The O,O, dialkyl phosphordithioic acid and an epoxide, hydroxyester or diol are then reacted as follows:

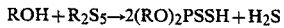

II

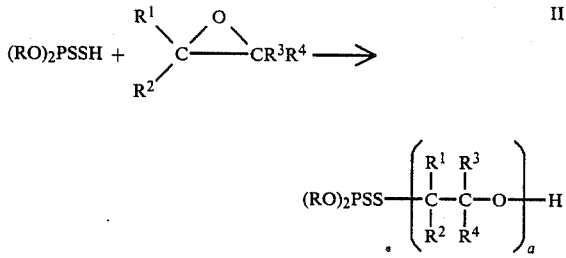

where "a" ranges between 1 to 10 and where $R^1$, $R^2$, $R^3$, and $R^4$ are hydrogens or $C_1$ to $C_{30}$ hydrocarbyl groups, and optionally contain sulfur, nitrogen, oxygen, or phosphorus. Although ethylene oxide, butylene oxide, and cyclohexene oxide in particular can be used, preferred are propylene oxide and butylene oxide.

The resulting product is then reacted with a hydroxybearing component and a borate such as boric acid.

III

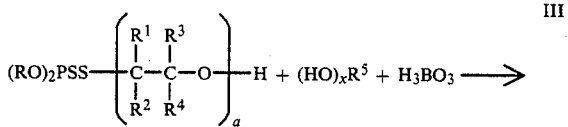

-continued

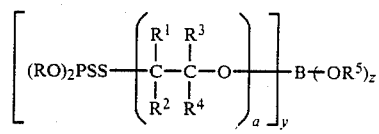

where $R^5$ is a $C_1$–$C_{30}$ hydrocarbyl group and optionally contains ester, amide or oxygen, nitrogen and/or sulfur groups, x is 1 to 10, y and z are integers and $y+z=3$.

The hydroxybearing compound can be a diol or mixture of diols such as 1,2-dodecanediol, 1,2-hexadecanediol, 1,2-octadecandiol, glycerol monooleate, glycerol dioleate, glycerol monostearate, glycerol monomyristate, sorbitan monooleate, and similar hydroxyl-containing species.

It is preferred to react the materials in the stochiometric ratios indicated in the previous equation although less than molar quantities or greater than molar quantities of a boronating agent can be use. Boric acid is the boronating agent of choice, although other boron compounds such as metaborates, trialkylborates or other suitable boronating agents can be employed. An excess of boronating agent can be used and is often preferred.

The reaction are all conducted at a temperature between about $-10°$ C. and about $250°$ C. for a period of between 1 and 48 hours. Preferably the reaction designated II above is conducted at a temperature of between $-30°$ C. and $60°$ C. and the reaction designated III at $50°$ C. to $250°$ C. The desired reaction product separates as a liquid that can be then decanted from the remaining reaction mixture. In preparing the lubricant composition of this invention it desirable to use the additive in a concentration of between 0.001% and 10% by weight of the total composition, although it is preferred to use between 0.1% to 3%. Greater concentrations can, of course, be used if such is desirable.

Of particular significance is the ability of the additives of this invention to improve a variety of properties of a lubricant composition. They include the improved wear resistance or friction qualities of lubricated parts and improved resistance to oxidation and corrosion of oleaginous materials in lubricating media. These media preferably comprise liquid oils, in the form of either a mineral oil or a snythetic oil or mixtures thereof, but also may be a grease in which any of the aforementioned oils are employed as a vehicle. In general, mineral oils, both paraffinic, naphthenic and mixtures thereof, employed as the lubricant, or grease vehicle, may be of any suitable lubricating viscosity range, as for example, from about 45 SUS at 100° F. to about 6000 SUS at 100° F., and preferably, from about 50 to about 250 SUS at 210° F. These oils may have viscosity indexes ranging to about 100 or higher preferably from about 70 to about 95. The average molecular weights of these oils may range from about 250 to about 800. Where the lubricant is to be employed in the form of a grease, the lubricating oil is generally employed in an amount sufficient to balance the total grease composition, after accounting for the desired quantity of the thickening agent, and other additive components to be included in the grease formulation. A wide variety of thickening agents can be used in the grease of this invention. Included among the thickening agents are alkali and alkaline earth metal soaps of fatty acids and fatty materials having from about 12 to about 30 carbon atoms per molecule. The metals are typified by sodium, lithium, calcium and barium. Fatty materials are illustrated by stearic acid, hydroxystearic acid, stearin, cottonseed oil acids, oleic acid, palmitic acid, myristic acid and hydrogenated fish oils. Other thickening agents include salt and salt-soap complexes as calcium stearate-acetate (U.S. Pat. No. 2,197,263); barium stearate acetate (U.S. Pat. No. 2,564,561); calcium stearate-caprylate-acetate complexes (U.S. Pat. No. 2,999,065); calcium caprylate-acetate (U.S. Pat. No. 2,999,066); and calcium salts and soaps of low-, intermediate- and high-molecular weight acids and of nut oil acids. In general, grease thickeners may be employed which do not melt and dissolve when used at the required temperature within a particular environment; however, in all other respects, any material which is normally employed for thickening or gelling hydrocarbon fluids for forming grease can be used in preparing the aforementioned improved grease in accordance with the present invention.

In instances where synthetic oils, or synthetic oils employed as the vehicle for the grease, are desired in preference to mineral oils, or in combination therewith, various compounds of this type may be successfully utilized. Typical synthetic vehicles include polyisobutylene, polybutenes, hydrogenated polydecenes, polypropylene glycol, polyethylene glycol, trimethylol propane esters, neopentyl and pentaerythritol esters, di(2-ethylhexyl) sebacate, di(2-ethylhexyl) adipate, dibutyl phthalate, fluorocarbons, silicate esters, silanes, esters of phosphorus-containing acids, liquid ureas, ferrocene derivatives, hydrogenated synthetic oils, chain-type polyphenyls, siloxanes and silicones (polysiloxanes), alkyl-substituted diphenyl ethers typified by a butyl-substituted bis(p-phenoxy phenyl) ether, phenoxy phenylethers.

It is to be understood that the compositions contemplated herein can also contain other materials. For example, other corrosion inhibitors, extreme pressure agents, anitwear agents, defoamants, detergents, dispersants, and the like can be used. These materials do not detract from the value of the compositions of this invention. Rather the materials serve to impart their customary properties to the particular compositions in which they are incorporated.

EXAMPLES

Example 1

Propoxylated Di-2-Ethylhexylphosphorodithioic Acid

Approximately 708.6 grams of di-2-ethylhexylphosphorodithioic acid (Stauffer Chemical Company) was charged into a one-liter flask and 116.5 grams (2.0 mole) propylene oxide were slowly added over a course of two hours. The reaction temperature was controlled at about or below 40° C. At the end of the addition, the color of the mixture changed from dark-green to light-yellow. The mixture weighed approximately 825 grams.

Example 2

Borated Mixed Glycerol Monooleate/s-2 Hydroxypropyl O,O-di-2-Ethylhexylphosphorodithioate Approximately 178.1 grams of commercial glycerol monooleate (Stepan Company), 31 grams boric acid, 206 grams of the product from Example 1 and 200 milliliters toluene were mixed in a one-liter, four-neck reactor equipped with thermometer, nitrogen gas sparger, Dean-Stark trap condenser, and agitator. The mixture was refluxed (113°±2° C.) over a period of three hours. A total volume of 22.8 milliliters of water was collected in the Dean-Stark trap.

An additional hour of heating produced no more water of reaction. The toluene was removed by distillation leaving about 392 grams of low-viscosity brown liquid product.

Example 3

Borated Mixed Glycol Monooleate/Propoxylated O,O-di-2-Ethylhexylphosphorodithioate (Using Higher Boric Acid Charge)

Approximately 178 grams glycerol monooleate, 93 grams boric acid, 206 grams of the product from Example 1 and 200 milliliters of toluene were mixed in a one-liter reactor with a nitrogen blanket. The mixture was heated and refluxed at 115°±2° C. over a course of 10 hours. A volume of 41.5 milliliters of water was collected in the Dean-Stark trap. Refluxing was continued for two more hours until $H_2O$ evolution ceased. The mixture was diluted with 300 milliliter extra toluene when it had cooled to below 50° C. The unreacted solids were then removed by filtration. The yellow-brown filtrate was returned to a reactor and toluene was removed under reduced pressure at 110°–115° C. A yield of 370 grams of brown liquid was obtained.

The hydroxyester/phosphorodithioate-derived alcohol borates from the examples were blended into fully formulated oils and evaluated for oxidative stability. Basically, in the test the lubricant is subjected to a stream of air which is bubbled through at a rate of 5 liters per hour at 325° F. for 40 hours (Table 1), 260° F. for 80 hours (Table 2), and 375° F. for 24 hours (Table 3). Present in the composition are samples of metals commonly used in engine construction, namely, iron, copper, aluminum and lead. See U.S. Pat. No. 3,682,980, incorporated herein by reference for further details of the test. Reductions in viscosity increase or limiting of neutralization number (or both) show effective control.

TABLE 1

| CATALYTIC OXIDATION TEST | | | |
|---|---|---|---|
| Item | Additive Conc. (Wt. %) | Percent Change in Kinematic Viscosity | Sludge |
| Base Oil (150 second, fully formulated, solvent refined paraffinic bright oil containing defoamant/demulsifier/antiwear/anticorrosion/EP/antirust performance package | 0 | 30.61 | Nil |
| Example 2 | 1.0 | 26.67 | Nil |

TABLE 2

| CATALYTIC OXIDATION TEST | | | | |
|---|---|---|---|---|
| Item | Additive Conc. (Wt. %) | Percent Change in Acid Number | Percent Change in Kinematic Viscosity | Sludge |
| Base Oil (150 second, fully formulated, solvent refined paraffinic bright oil containing defoamant/demulsifier/antiwear/anticorrosion/EP/antirust performance package | 0 | 0.01 | 6.48 | Nil |

TABLE 2-continued

| | CATALYTIC OXIDATION TEST | | | |
|---|---|---|---|---|
| Item | Additive Conc. (Wt. %) | Percent Change in Acid Number | Percent Change in Kinematic Viscosity | Sludge |
| Example 2 | 1.0 | 0.11 | 6.46 | Nil |
| Example 3 | 1.0 | −0.41 | 6.42 | Nil |

TABLE 3

| | CATALYTIC OXIDATION TEST | | | |
|---|---|---|---|---|
| Item | Additive Conc. (Wt. %) | Percent Change in Acid Number | Percent Change in Kinematic Viscosity | Sludge |
| Base Oil (150 second, fully formulated, solvent refined paraffinic bright oil containing defoamant/ demulsifier/antiwear/ anticorrosion/EP/ antirust performance package | — | 6.53 | 177.9 | Medium |
| Example 2 | 1.0 | 4.29 | 125.6 | Light |
| Example 3 | 1.0 | 4.08 | 101.2 | Medium |

Table 4 below shows the improved wear resistance of these additives when tested in a Shell 4-ball wear tester.

TABLE 4

| | Four-Ball Test | | | |
|---|---|---|---|---|
| | Wear Scar Diameter in MM, 30 Minute Test 60 kg Load | | | |
| Item | 1000 RPM 200° F. | 2000 RPM 200° F. | 1000 RPM 300° F. | 2000 RPM 300° F. |
| Base Oil (80% Solvent Paraffinic Bright, 20% Solvent Paraffinic Neutral Mineral Oils) No additive from the Examples | 1.91 | 2.63 | 1.95 | 2.50 |
| 1% Example 2 in above Base Oil | 0.77 | 1.13 | 0.86 | 1.15 |
| 1% Example 3 in above Base Oil | 0.75 | 1.43 | 0.81 | 1.38 |

As an be seen from the above wear test results, the products described exhibit considerable antiwear activity.

What is claimed is:

1. The reaction product produced by: (a) reacting a phosphorodithioic acid and an epoxide, hydroxyester, or diol resulting in an intermediate product; and (b) reacting the intermediate product with a borating compound and a hydroxy-bearing compound to produce the desired reaction product, each reaction being conducted at a temperature between about 10° C. and about 150° C. for a period of between about 1 and about 48 hours in a proportion of reactants of about 1 mole of each.

2. The reaction product of claim 1 wherein the phosphorodithioic acid has the formula:

$(RO)_2PSSH$ where R is a $C_3$ to $C_{30}$ hydrocarbyl or oxyhydrocarbylene group, or mixtures thereof.

3. The reaction product of claim 1 wherein the epoxide has the structural formula:

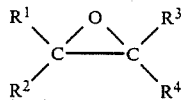

where $R^1$, $R^2$, $R_3$, and $R^4$ are hydrogen or a $C_1$ to $C_{30}$ hydrocarbyl group optionally containing sulfur, nitrogen, or oxygen atoms.

4. The reaction product of claim 1 wherein the hydroxy-bearing compound has the structural formula:

$(HO)_xR^5$ where $R^5$ is hydrogen or $C_1$ to $C_{30}$ hydrocarbyl group and optionally contains ester, amide, oxygen, nitrogen and/or sulfur groups, and x is 1 to 10.

5. The reaction product of claim 1 wherein the borating agent is selected from the group consisting of boric acid, methaborates and trialkylborates.

6. The product produced by reacting:
(a) a phosphorodithioic acid of the formula:

$(RO)_2PSSH$ where R is a $C_3$ to $C_{30}$ hydrocarbyl or oxyhydrocarbylene group, or mixtures thereof with an epoxide of the formula:

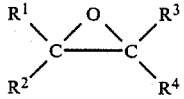

where $R^1$, $R^2$, $R^3$, and $R^4$ are hydrogen or a $C_1$ to $C_{30}$ hydrocarbyl group optionally containing sulfur, nitrogen, or oxygen atoms, to obtain the intermediate product or mixture:

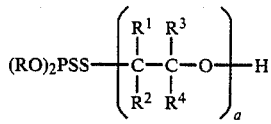

where a is an integer from 1 to 10,
(b) reacting the intermediate product from (a) with a borating compound and a hydroxy bearing compound of the formula:

$(HO)_xR^5$ to produce the compound of the structural formula:

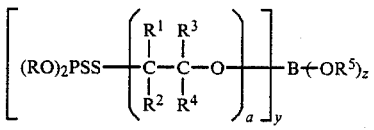

where $R^5$ is hydrogen or a $C_1$ to $C_{30}$ hydrocarbyl group and optionally contains ester, amide or oxygen, nitrogen and/or sulfur groups, x is 0 to 10, y and z are integers and $y+z=3$, each reaction being conducted at a temperature between about $-10°$ C. and about 250° C. for a period of between about 1 and about 48 hours in a proportion of reactants of about 1 mole each.

7. The reaction product of claim 5 where the reaction in (a) is carried out at a temperature between about $-10°$ C. and about 60° C. and the reaction of (b) is carried out at a temperature of about 50° C. and about 250° C.

8. The reaction product of claim 5 wherein the borating compound is boric acid ($H_3BO_3$).

9. The reaction product of claim 5 wherein the borating compound is selected from the group consisting of metaborates and trialkylborates.

10. The reaction product of claim 5 wherein $R^1$, $R^2$, $R^3$, and $R^4$ are selected from the group consisting of hydrogen and $C_1$ to $C_{30}$ hydrocarbyl groups.

11. The reaction product of claim 5 wherein $R^5$ is selected from the group consisting of $C_1$ to $C_{30}$ hydrocarbyl groups.

12. The reaction product of claim 5 wherein the phosphorodithioic acid is made by reacting di-2-ethhylhexylphosphorodithioic acid and propylene oxide.

13. The reaction product of claim 5 wherein the epoxide is propylene oxide.

14. The reaction product of claim 5 wherein the hydroxy-bearing compound of (b) is glycerol monooleate.

15. The reaction product of claim 5 wherein the intermediate product of (a) is the reaction product of di-2-ethylhexylphosphorodithioic acid and propylene oxide.

16. The reaction product of claim 5 wherein the intermediate product of (a) is the reaction product of di-2-ethylhexyl-phosphorodithioic acid, and propylene oxide and the hydroxy-bearing compound of (b) is glycerol monooleate.

17. A lubricant composition comprising a lubricant and between about 0.001% and about 10% by weight of the composition of claim 1.

18. A lubricant composition comprising a lubricant and between about 0.001% and about 10% by weight of the composition of claim 2.

19. A lubricant composition comprising a lubricant and between about 0.001% and about 10% by weight of the composition of claim 3.

20. A lubricant composition comprising a lubricant and between about 0.001% and about 10% by weight of the composition of claim 4.

21. A lubricant composition comprising a lubricant and between about 0.001% and about 10% of the composition of claim 5.

22. A lubricant composition comprising a lubricant and between about 0.001% and about 10% by weight of the composition of claim 6.

23. A lubricant composition comprising a lubricant and between about 0.001% and about 10% weight of the composition of claim 7.

24. A lubricant composition comprising a lubricant and between about 0.001% and about 10% weight of the composition of claim 10.

25. A lubricant composition comprising as lubricant selected from the group consisting of mineral oil, synthetic oils, and greases, and between about 0.001% and about 10% by weight of the composition of claim 5.

26. A lubricant composition comprising a major proportion of a lubricant and between about 0.001% and about 1% by weight of the composition of claim 5.

27. The reaction product of claim 5 wherein the mole ratio of borating agent to the other reactants is greater than 1.

28. The lubricant composition of claim 22 where the reaction in (a) is carried out at a temperature between about $-10°$ C. and about 60° C. and the reaction of (b) is carried out at a temperature of about 50° C. and about 250° C.

29. The lubricant composition of claim 22 wherein the borating compound is boric acid ($H_3BO_3$).

30. The lubricant composition of claim 22 wherein the borating compound is selected from the group consisting of metaborates and trialkylborates.

31. The lubricant composition of claim 22 wherein $R^1$, $R^2$, $R^3$, and $R^4$ are selected from the group consisting of hydrogen, and $C_1$ to $C_{20}$ hydrocarbyl groups.

32. The lubricant composition of claim 22 wherein $R^5$ is selected from the group consisting of $C_1$ to $C_{30}$ hydrocarbyl groups.

33. The lubricant composition of claim 22 wherein the phosphorodithioic acid is made by reacting di-2-ethylhexylphosphorodithioic acid and propylene oxide.

34. The lubricant composition of claim 22 wherein the epoxide is propylene oxide.

35. The lubricant composition of claim 22 wherein the hydroxy-bearing compound of (b) is glycerol monooleate.

36. The lubricant composition of claim 22 wherein the intermediate product of (a) is the reaction product of di-2-ethylhexylphosphorodithioic acid, and propylene oxide.

37. The lubricant composition of claim 22 wherein the intermediate product of (a) is the reaction product of di-2-ethylhexylphosphorodithioic acid and propylene oxide and the hydroxy-bearing compound of (b) is glycerol monooleate.

38. The lubricant composition of claim 22 wherein the lubricant is a grease.

39. The lubricant composition of claim 22 containing additional phosphorus and sulfur moities.

40. A lubricant composition comprising a lubricant and between about 0.001% and about 10% by weight of the composition of an additive for increasing the resistance to oxidation of the lubricant and increasing its wear reducing characteristics said additive comprising the product produced by reacting:

(a) a phosphorodithioic acid of the formula:

$(RO)_2PSSH$ where R is a $C_3$ to $C_{30}$ hydrocarbyl or oxyhydrocarbylene, or mixtures thereof with an epoxide of the formula:

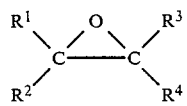

where $R^1$, $R^2$, $R^3$, and $R^4$ are hydrogen or $C_1$ to $C_{30}$ hydrocarbyl groups, to obtain the intermediate product:

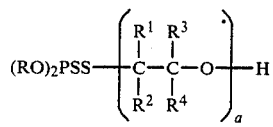

where a is an integer from 1 to 10, (b) reacting the intermediate product from (a) with a borating compound and a hydroxy-bearing compound of the formula:

where $R^5$ is hydrogen or $C_1$ to $C_{30}$ hydrocarbyl group and optionally contains ester, amide, oxygen, nitrogen and/or sulfur groups, and x is 0 to 10 to produce the compound of the structural formula:

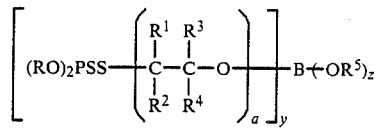

where y and z are integers and $z+z=3$ each reaction being conducted at a temperature between about $-10°$ C. and about 250° C. for a period of between about 1 and about 48 hours in a ratio of reactants of about 1 mole of each.

* * * * *